US011006898B2

(12) United States Patent
Yamada et al.

(10) Patent No.: US 11,006,898 B2
(45) Date of Patent: May 18, 2021

(54) BIOLOGICAL INFORMATION MEASUREMENT APPARATUS, METHOD FOR CONTROLLING THE SAME, AND RECORDING MEDIUM

(71) Applicant: Alps Alpine Co., Ltd., Tokyo (JP)

(72) Inventors: Yukimitsu Yamada, Miyagi-ken (JP); Daisuke Takai, Miyagi-ken (JP); Toshiki Nakamura, Miyagi-ken (JP)

(73) Assignee: Alps Alpine Co., Ltd., Tokyo (JP)

( * ) Notice: Subject to any disclaimer, the term of this patent is extended or adjusted under 35 U.S.C. 154(b) by 69 days.

(21) Appl. No.: 16/452,378

(22) Filed: Jun. 25, 2019

(65) Prior Publication Data

US 2019/0307402 A1   Oct. 10, 2019

Related U.S. Application Data

(63) Continuation of application No. PCT/JP2018/002547, filed on Jan. 26, 2018.

(30) Foreign Application Priority Data

Feb. 17, 2017   (JP) .............................. JP2017-028536

(51) Int. Cl.

| *A61B 5/25* | (2021.01) |
| *A61B 5/296* | (2021.01) |
| *A61B 5/389* | (2021.01) |
| *A61B 5/398* | (2021.01) |
| *A61B 5/00* | (2006.01) |

(Continued)

(52) U.S. Cl.

CPC .............. *A61B 5/6844* (2013.01); *A61B 5/25* (2021.01); *A61B 5/296* (2021.01); *A61B 5/318* (2021.01);

(Continued)

(58) Field of Classification Search
CPC ... A61B 5/6844; A61B 5/0408; A61B 5/0492; A61B 5/0402; A61B 5/25; A61B 5/296;

(Continued)

(56) References Cited

U.S. PATENT DOCUMENTS

| 5,817,031 A | 10/1998 | Masuo et al. |
| 2012/0029336 A1* | 2/2012 | Terada ................... A61B 5/291 |
| | | 600/383 |

(Continued)

FOREIGN PATENT DOCUMENTS

| JP | H8-154911 | 6/1996 |
| JP | 2004-313494 | 11/2004 |

(Continued)

OTHER PUBLICATIONS

International Search Report for International Application No. PCT/JP2018/002547 dated Jan. 5, 2018.

*Primary Examiner* — Carl H Layno
*Assistant Examiner* — Anh-Khoa N Dinh
(74) *Attorney, Agent, or Firm* — Beyer Law Group LLP

(57) ABSTRACT

The biological information measurement apparatus includes a first signal applying unit which applies a first applying signal to electrodes at the time of the measurement of biological information, a biological information measurement unit which measures biological information based on detection signals of the electrodes at the time of the measurement of biological information, a second signal applying unit which applies a second applying signal to the electrodes at a time of detection of an attached state, and an attached state detection unit which detects an attached state based on the detection signals at the time of the detection of an attached state. At least some of the electrodes at the time of the measurement of biological information is identical with at least some of the electrodes at the time of the detection of an attached state.

18 Claims, 11 Drawing Sheets

(51) Int. Cl.
*H04Q 9/00* (2006.01)
*A61B 1/05* (2006.01)
*A61B 5/26* (2021.01)
*A61B 5/318* (2021.01)

(52) U.S. Cl.
CPC ............ *H04Q 9/00* (2013.01); *A61B 2562/04* (2013.01); *H04Q 2209/82* (2013.01); *H04Q 2209/84* (2013.01)

(58) Field of Classification Search
CPC ......... A61B 5/318; A61B 5/389; A61B 5/398; A61B 5/0531; A61B 5/26; A61B 5/251; A61B 5/683; A61B 5/688; A61B 5/685; A61B 5/686; H04Q 9/00; H04Q 2562/04; H04Q 2209/82; H04Q 2209/84; H04Q 2209/86; H04Q 2209/40; H04Q 2209/823
See application file for complete search history.

(56) References Cited

U.S. PATENT DOCUMENTS

2013/0204100 A1\* 8/2013 Acquista ............ A61B 5/02028
600/301
2014/0155767 A1\* 6/2014 Fukuda .............. A61B 5/02125
600/485
2017/0086699 A1 3/2017 Shirai

FOREIGN PATENT DOCUMENTS

| JP | 2007/209430 | 8/2007 |
| JP | 2009-261419 | 11/2009 |
| JP | 2014-108141 | 6/2014 |
| WO | 2016/125214 | 8/1916 |
| WO | 2011/074186 | 6/2011 |

\* cited by examiner

BIOLOGICAL INFORMATION MEASUREMENT APPARATUS, METHOD FOR CONTROLLING THE SAME, AND RECORDING MEDIUM

CLAIM OF PRIORITY

This application is a Continuation of International Application No. PCT/JP2018/002547 filed on Jan. 26, 2018, which claims benefit of Japanese Patent Application No. 2017-028536 filed on Feb. 17, 2017. The entire contents of each application noted above are hereby incorporated by reference.

BACKGROUND OF THE INVENTION

1. Field of the Invention

The present invention relates to a biological information measurement apparatus, a method for controlling the biological information measurement apparatus, and a recording medium for storing program for controlling the biological information measurement apparatus.

2. Description of the Related Art

In general, a biological information measurement apparatus which is attached to a living body and which measures biological information, such as electrocardiographic information of cardiac activity of the living body, has been developed. Japanese Unexamined Patent Application Publication No. 2014-108141 discloses an electrocardiographic information measurement apparatus as one type of biological information measurement apparatus. The electrocardiographic information measurement apparatus disclosed in Japanese Unexamined Patent Application Publication No. 2014-108141 measures an electrocardiographic waveform by attaching electrocardiographic electrodes which are disposed on a surface of the electrocardiographic information measurement apparatus to a breast portion. A person is required to check whether the electrocardiographic electrodes are firmly attached so that electrocardiographic information is measured by the electrocardiographic information measurement apparatus disclosed in Japanese Unexamined Patent Application Publication No. 2014-108141 with high accuracy.

Japanese Unexamined Patent Application Publication No. 2004-313494 discloses an automatic attachment recognition apparatus which recognizes attachment, to a living body, of a detection device which detects a biological signal of a living body. The automatic attachment recognition apparatus disclosed in Japanese Unexamined Patent Application Publication No. 2004-313494 has two electrodes which are brought into contact with the living body when the detection device is attached to the living body. The automatic attachment recognition apparatus recognizes that the detection device has been attached to the living body based on a high-frequency signal supplied between the two electrodes.

SUMMARY OF THE INVENTION

However, in the automatic attachment recognition apparatus disclosed in Japanese Unexamined Patent Application Publication No. 2004-313494, the electrodes are required to be disposed separately from the detection device, and therefore, the apparatus has a large configuration. Note that a shared electrode or a detailed configuration of a shared electrode is not mentioned in Japanese Unexamined Patent Application Publication No. 2004-313494.

The present invention provides a biological information measurement apparatus which measures biological information with high accuracy with a simple configuration and less operation by a user, a method for controlling the biological information measurement apparatus, and a recording medium for storing a program for controlling the biological information measurement apparatus.

According to an aspect of the present invention, a biological information measurement apparatus includes a plurality of electrodes to be attached to a living body, a first signal applying unit configured to apply a first applying signal to at least one of the electrodes at a time of measurement of biological information based on an electric signal obtained from the living body, a biological information measurement unit configured to measure the biological information at the time of the measurement of biological information based on a detection signal detected by at least one of the electrodes, a second signal applying unit configured to apply a second applying signal to at least one of the electrodes at a time of detection of an attached state of at least one of the electrodes relative to the living body, and an attached state detection unit configured to detect the attached state based on the detection signal detected at the time of the detection of an attached state of at least one of the electrodes which is different from the electrode to which the second applying signal is applied. At least some of the at least one of the electrodes to which the first applying signal is applied at the time of the measurement of biological information and the at least one of the electrodes in which the detection signal is detected at the time of the measurement of biological information are identical with at least some of the at least one of the electrodes to which the second applying signal is applied at the time of the detection of an attached state and the at least one of the electrodes in which the detection signal is detected at the time of the detection of an attached state.

With this configuration, in the biological information measurement apparatus in which the first applying signal is applied to the living body when the biological information is measured and the second applying signal is applied to the living body when the attached state is detected, the electrodes may be shared at the time of the biological information measurement and the attached state detection, and therefore, the attached state may be automatically detected with a simple configuration when compared with a case where different electrodes are provided. Accordingly, the biological information may be measured with high accuracy with a simple configuration and less operation by a user. By detecting an attached state, reliability of measurement data becomes high, and therefore, biological information may be measured with high accuracy with a simple configuration and less operation by a user.

The biological information measurement apparatus may further include a switching unit configured to perform switching among at least some of connections among at least one of the electrodes, the first signal applying unit, and the second signal applying unit. The plurality of electrodes may include a first electrode. The switching unit may perform switching between a first connection state in which the first applying signal is applied to the first electrode at the time of the measurement of biological information and a second connection state in which the second applying signal is applied to the first electrode at the time of the detection of an attached state.

With this simple configuration in which the first connection state and the second connection state are switched from one to another by the switching units, the electrodes may be used in common at the time of the biological information measurement and the attached state detection.

The biological information measurement apparatus may further include a relation detection unit configured to detect one or a plurality of relation signals indicating a relative relationship among a plurality of input electric signals. The plurality of electrodes may include a second electrode. The switching unit may perform switching among at least some of connections among at least one of the electrodes, the first signal applying unit, the second signal applying unit, and the relation detection unit. The detection signal detected by the first electrode and the detection signal detected by the second electrode may be supplied to the relation detection unit in the first connection state. The first applying signal and the detection signal detected by the second electrode may be supplied to the relation detection unit in the second connection state. The relation detection unit may detect the relation signal indicating the relative relationship between the detection signal detected by the first electrode and the detection signal detected by the second electrode at the time of the measurement of biological information. The relation detection unit may detect the relation signal indicating the relative relationship between the first applying signal and the detection signal detected by the second electrode at the time of the detection of an attached state. The biological information measurement unit may measure the biological information based on the relation signal detected by the relation detection unit at the time of the measurement of biological information. The attached state detection unit may detect the attached state based on the relation signal detected by the relation detection unit at the time of the detection of an attached state.

With this simple configuration in which the first connection state and the second connection state are switched from one to another by the switching units, the relation detection unit may be used in common at the time of the biological information measurement and the attached state detection.

In the biological information measurement apparatus, the second applying signal may include at least one combination of a period in which a low voltage value is applied and a period in which a high voltage value which is higher than the low voltage value is applied. The attached state detection unit may calculate a low voltage average value indicating an average value of the relation signals obtained when the low voltage value is applied and low voltage dispersion indicating dispersion of the relation signals obtained when the low voltage value is applied. The attached state detection unit may calculate a high voltage average value indicating an average value of the relation signals obtained when the high voltage value is applied and high voltage dispersion indicating dispersion of the relation signals obtained when the high voltage value is applied. The attached state detection unit may determine that an attached state is normal when a first condition indicating that the low voltage dispersion is smaller than a low voltage threshold value, a second condition indicating that the high voltage dispersion is smaller than a high voltage threshold value, and a third condition indicating that an absolute value of a difference between the low voltage average value and the high voltage average value is larger than an absolute threshold value are all satisfied. The attached state detection unit may determine that an attached state is abnormal when at least one of the first to third conditions is not satisfied.

With this configuration, the change of the relation signals in accordance with the second applying signal may be accurately determined when compared with a case where one of the first to third conditions is not used for the determination.

In the biological information measurement apparatus according to the present invention, the first applying signal may be a direct current voltage. The second applying signal may be a rectangular voltage. The attached state detection unit may detect the attached state based on one of a rising time and a falling time of a signal indicating a difference between the first applying signal and the detection signal at the time of the detection of an attached state.

With this configuration, the attached state may be detected with a simple configuration by detecting rounding of the detection signals which has passed through the living body from at least one of the rising time and the falling time of a signal indicating a difference between the first applying signal and the detection signals.

In the biological information measurement apparatus according to the present invention, the attached state detection unit may at least temporarily stop the measurement of biological information performed by the biological information measurement unit when the detection signal satisfies a condition corresponding to an abnormal attached state at the time of the detection of an attached state.

With this configuration, the measurement of biological information may be at least temporarily stopped based on the attached state, and therefore, unrequired measurement of biological information in an abnormal attached state may be avoided and wasteful power consumption may be suppressed.

In the biological information measurement apparatus according to the present invention, the attached state detection unit may start the measurement of biological information performed by the biological information measurement unit when the detection signal satisfies a condition corresponding to a normal detection state at the time of the detection of an attached state.

With this configuration, the measurement of biological information may be automatically started based on the attached state, and therefore, complicated operations to be performed by the user may be eliminated and usability may be enhanced.

In the biological information measurement apparatus according to the present invention, the second applying signal may have a signal waveform which is different from a signal waveform of a noise signal.

With this configuration, the attached states of the electrodes may be accurately detected without mistakenly recognizing the second applying signal as a noise signal.

According to an aspect of the present invention, a method for controlling a biological information measurement apparatus including a plurality of electrodes to be attached to a living body includes applying a first applying signal to at least one of the electrodes at a time of measurement of biological information based on an electric signal obtained from the living body, measuring the biological information at the time of the measurement of biological information based on a detection signal detected by at least one of the electrodes, applying a second applying signal to at least one of the electrodes at a time of detection of an attached state of at least one of the electrodes relative to the living body, and detecting the attached state based on the detection signal detected at the time of the detection of an attached state in at least one of the electrodes which is different from the electrode to which the second applying signal is applied. At least some of the at least one of the electrodes to which the first applying signal is applied at the time of the measurement of biological information and at the least one of the electrodes in which the detection signal is detected at the time of the measurement of biological information are identical with at least some of the at least one of the electrodes to which the second applying signal is applied at the time of the detection of an attached state and the at least one of the electrodes in which the detection signal is detected at the time of the detection of an attached state.

According to an aspect of the present invention, a non-transitory computer readable recoding medium storing a program for controlling a biological information measurement apparatus including a plurality of electrodes to be attached to a living body is provided. The program causes a computer to execute a process including applying a first applying signal to at least one of the electrodes at a time of measurement of biological information based on an electric signal obtained from the living body, measuring the biological information at the time of the measurement of biological information based on a detection signal detected by at least one of the electrodes, applying a second applying signal to at least one of the electrodes at a time of detection of an attached state of at least one of the electrodes relative to the living body, and detecting the attached state based on the detection signal detected at the time of the detection of an attached state in at least one of the electrodes which is different from the electrode to which the second applying signal is applied. At least some of the at least one of the electrodes to which the first applying signal is applied at the time of the measurement of biological information and the at least one of the electrodes in which the detection signal is detected at the time of the measurement of biological information are identical with at least some of the at least one of the electrodes to which the second applying signal is applied at the time of the detection of an attached state and the at least one of the electrodes in which the detection signal is detected at the time of the detection of an attached state.

DESCRIPTION OF THE PREFERRED EMBODIMENTS

Entire Configuration

Figure 1:
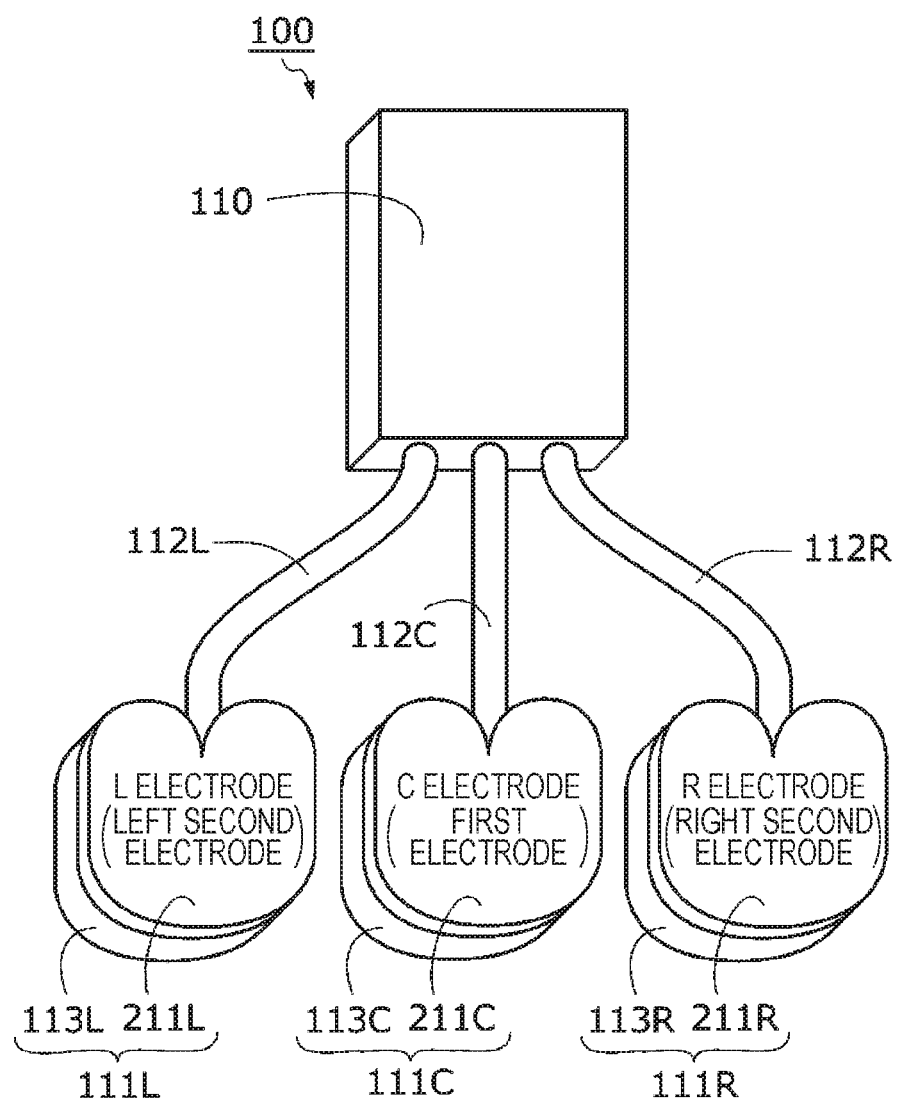
FIG. 1 is a diagram illustrating a configuration of a biological information measurement apparatus according to an embodiment of the present invention.

A biological information measurement apparatus according to an embodiment of the present invention will be described hereinafter. FIG. 1 is a diagram illustrating a configuration of a biological information measurement apparatus 100 according to an embodiment of the present invention. The biological information measurement apparatus 100 includes a control device 110, a C pad 111C, an L pad 111L, an R pad 111R, C wiring 112C, L wiring 112L, and R wiring 112R.

The C pad 111C includes a flat C insulator 113C and a flat first electrode 211C (which is also referred to as a "common electrode" and as a "C electrode 211C" hereinafter where appropriate) which is attached to one surface of the C insulator 113C. The L pad 111L includes a flat L insulator 113L and a left second electrode 211L (which is referred to as an "L electrode 211L" hereinafter where appropriate) which is attached to one surface of the L insulator 113L. The R pad 111R includes a flat R insulator 113R and a right second electrode 211R (which is referred to as an "R electrode 211R" hereinafter where appropriate) which is attached to one surface of the R insulator 113R. Hereinafter, when it is unnecessary to distinguish the C electrode 211C, the L electrode 211L, and the R electrode 211R from one another, the electrodes may be referred to as electrodes 211 where appropriate. The electrodes 211 are constituted by a conductive member, such as a metal member, and are externally exposed allowed to be brought into contact with a living body.

The control device 110 includes components which constitute the electric system described below. The C wiring 112C electrically connects the control device 110 and the C electrode 211C with each other. The L wiring 112L electrically connects the control device 110 and the L electrode 211L with each other. The R wiring 112R electrically connects the control device 110 and the R electrode 211R with each other.

The biological information measurement apparatus 100 performs biological information measurement by measuring information of a living body based on an electric signal obtained from the living body and performs attached state detection by detecting a state of attachment of at least one of the electrodes 211 to the living body. The living body is, for example, a person. The biological information is, for example, presented as an electrocardiogram. The biological information measurement apparatus 100 operates by using electricity from an incorporated battery (not illustrated).

The C electrode 211C, the L electrode 211L, and the R electrode 211R are disposed on the skin in the vicinity of the heart of a human body. The C electrode 211C is disposed between the L electrode 211L and the R electrode 211R, in a position closest to the heart. When the electrodes are appropriately attached to the living body, the L electrode 211L and the R electrode 211R are symmetrically disposed with respect to the C electrode 211C as the center. A voltage waveform between the C electrode 211C and the L electrode 211L is detected. Furthermore, a voltage waveform between the C electrode 211C and the R electrode 211R is detected. A difference between the two detected voltage waveforms indicates electrocardiographic information of the human body.

Control Device

Figure 2:
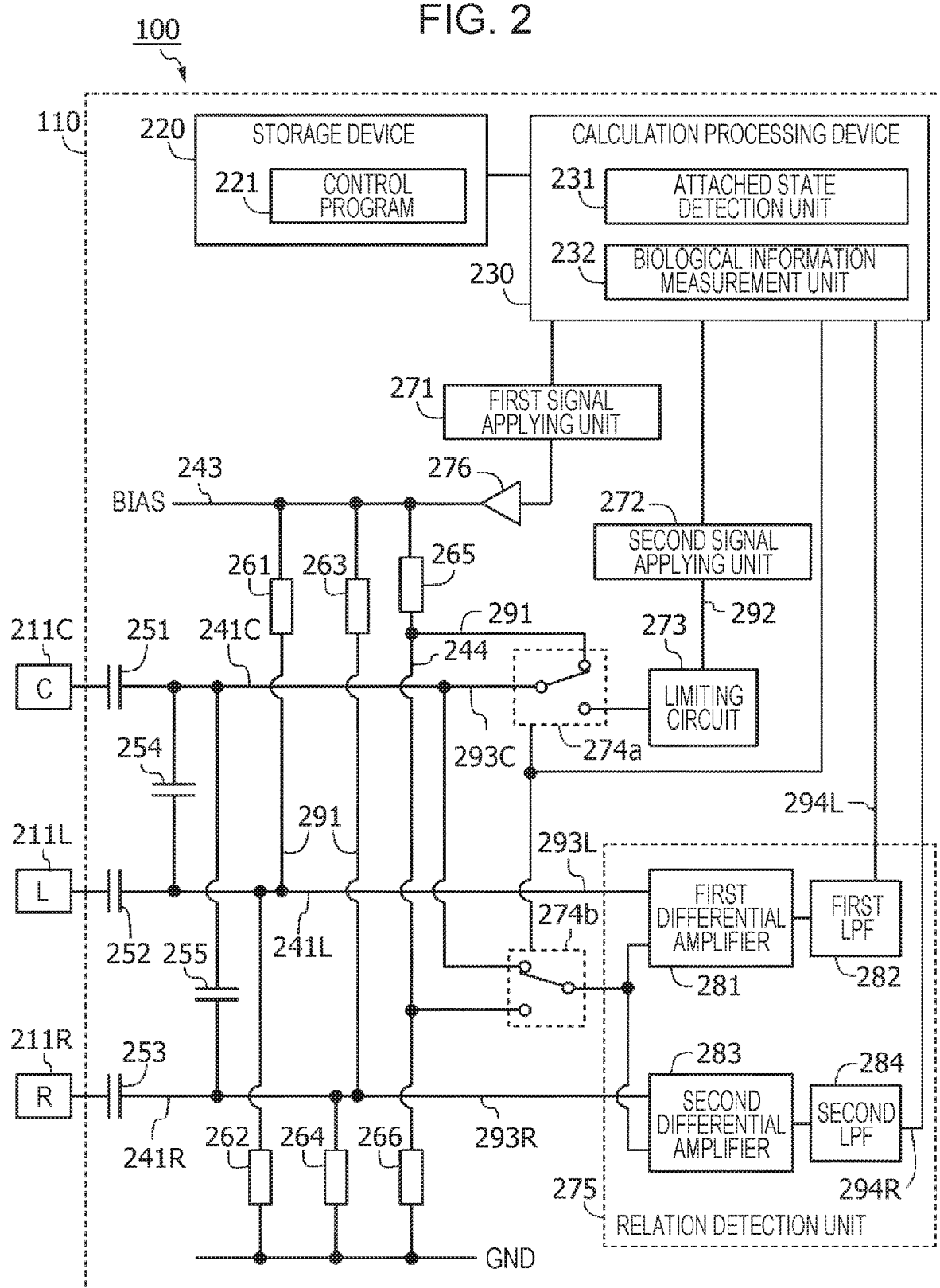
FIG. 2 is a diagram illustrating a configuration of a control system of the biological information measurement apparatus of FIG. 1 at a time of measurement of biological information.
Figure 3:
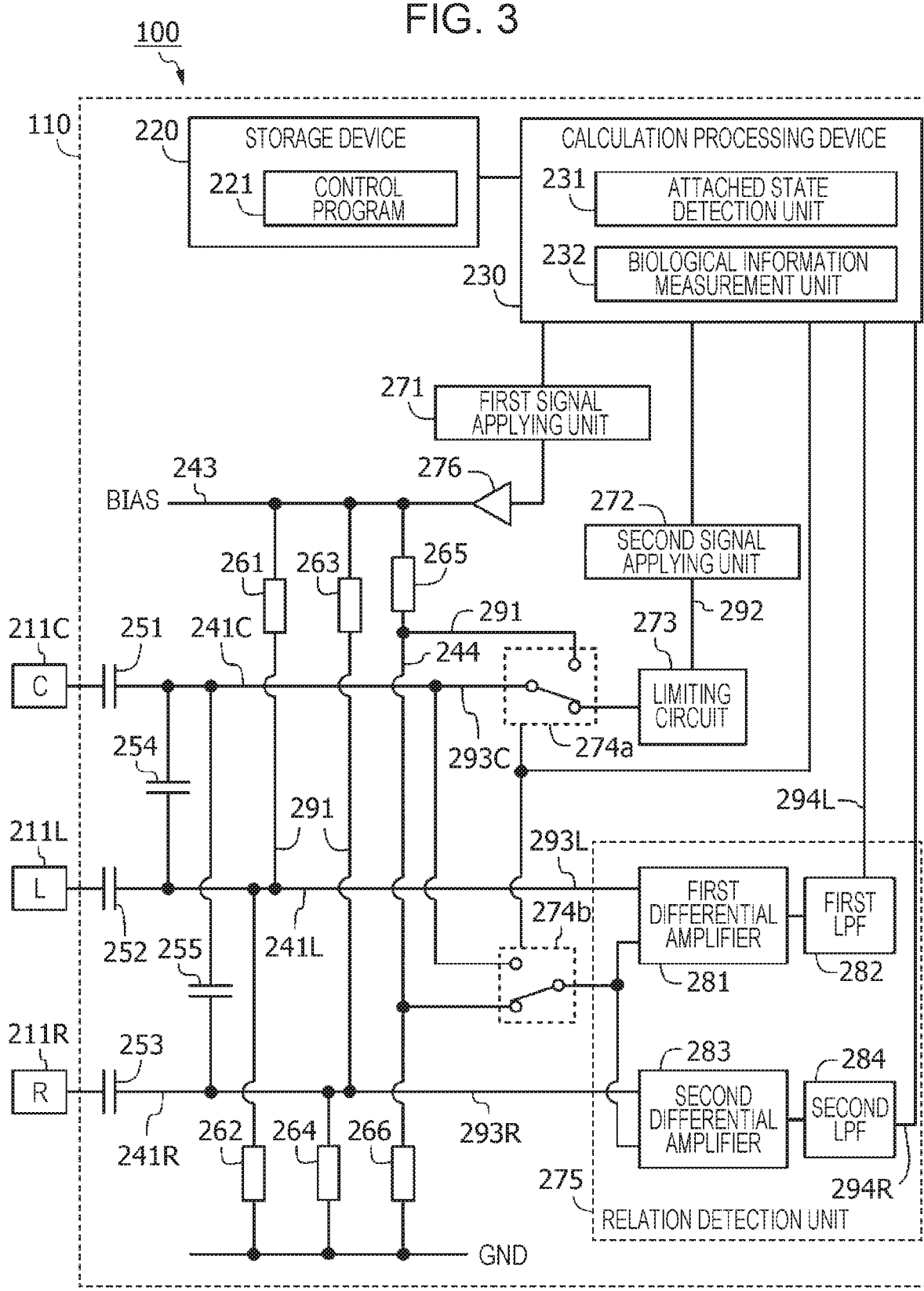
FIG. 3 is a diagram illustrating a configuration of the control system of the biological information measurement apparatus of FIG. 1 at a time of detection of an attached state.

FIG. 2 is a diagram illustrating a configuration of a control system of the biological information measurement apparatus 100 at a time of the biological information measurement. FIG. 3 is a diagram illustrating a configuration of the control system of the biological information measurement apparatus 100 at a time of detection of an attached state. As illustrated in FIG. 2, the control device 110 includes a storage device 220 and a calculation processing device 230.

The storage device 220 stores a control program 221. The control program 221 is read by the calculation processing device 230 and causes the calculation processing device 230 to implement a function of performing part of a method for controlling the biological information measurement apparatus 100 and other functions.

When the calculation processing device 230 executes the various functions, the storage device 220 stores required information where appropriate under the control of the calculation processing device 230. The storage device 220 is a non-transitory tangible storage medium. The storage device 220 includes a read-only memory (ROM) and a random access memory (RAM). The storage device 220 is a volatile or nonvolatile storage medium. The storage device 220 may be detachable or non-detachable.

The calculation processing device 230 functions as an attached state detection unit 231 and a biological information measurement unit 232 by reading and executing the control program 221 stored in the storage device 220. Although the calculation processing device 230 of this embodiment is a general computer, the calculation processing device 230 may be an application specific integrated circuit (ASIC) or other type of circuit implementing the functions described in this embodiment.

The operation of the attached state detection unit 231 and the biological information measurement unit 232 will be described hereinafter in detail.

As illustrated in FIG. 2, the control device 110 includes a C node 241C, an L node 241L, an R node 241R, a power source node 243, a relay node 244, first to fifth capacitors 251 to 255, first to sixth resistors 261 to 266, a first signal applying unit 271, a second signal applying unit 272, and a limiting circuit 273. The control device 110 further includes first and second switching units 274a and 274b (which are referred to as switching units 274 where appropriate hereinafter when it is unnecessary to distinguish the units from each other), a relation detection unit 275, and a buffer 276.

The first capacitor 251 is connected between the C electrode 211C and the C node 241C. The second capacitor 252 is connected between the L electrode 211L and the L node 241L. The third capacitor 253 is connected between the R electrode 211R and the R node 241R. The fourth capacitor 254 is connected between the C node 241C and the L node 241L. The fifth capacitor 255 is connected between the C node 241C and the R node 241R.

A case where an electric signal is applied to the C electrode 211C, the L electrode 211L, and the R electrode 211R means that an electric signal is applied to the C node 241C, the L node 241L, and the R node 241R.

The first resistor 261 is connected between the power source node 243 and the L node 241L. The second resistor 262 is connected between a ground voltage (GND) of an approximately 0 V and the L node 241L. The third resistor 263 is connected between the power source node 243 and the R node 241R. The fourth resistor 264 is connected between the GND and the R node 241R. The fifth resistor 265 is connected between the power source node 243 and the relay node 244. The sixth resistor 266 is connected between the GND and the relay node 244.

The first signal applying unit 271 supplies a direct current voltage (BIAS) of 1.5 V to the power source node 243 via the buffer 276 in accordance with an instruction issued by the calculation processing device 230. Partial pressures observed in the L node 241L, the R node 241R, and the relay node 244 caused by influence of the direct current voltage BIAS supplied between the power source node 243 and the GND are referred to as first applying signals 291.

Resistance values of the first to sixth resistors 261 to 266 are determined such that all the first applying signals 291 have 1.2 V. Voltages applied from the first signal applying unit 271 to the L node 241L, the R node 241R, and the relay node 244 are used as electric signals to be applied from the first signal applying unit 271 to the L electrode 211L, the R electrode 211R, and the C electrode 211C, respectively. Specifically, the first signal applying unit 271 applies the first applying signal 291 to at least one of the electrodes 211.

The second signal applying unit 272 outputs a second applying signal 292 which is a rectangular voltage to the limiting circuit 273 in accordance with an instruction issued by the calculation processing device 230. The second signal applying unit 272 applies the second applying signal 292 to at least one of the electrodes 211 as described below. The second applying signal 292 has a signal waveform which is different from that of a noise signal generated when the measurement of biological information (FIG. 2) or the detection of an attached state (FIG. 3) is performed.

The limiting circuit 273 is connected between the second signal applying unit 272 and the first switching unit 274a. The limiting circuit 273 limits the second applying signal 292 so that any current hazardous to human body is not supplied.

A voltage observed in the C node 241C at the time of the measurement of biological information (FIG. 2) is used as an electric signal detected by the C electrode 211C and is referred to as a "C detection signal 293C". A voltage observed in the L node 241L at the time of the measurement of biological information (FIG. 2) and at the time of the detection of an attached state (FIG. 3) is used as an electric signal detected by the L electrode 211L and is referred to as an "L detection signal 293L". A voltage observed in the R node 241R at the time of the measurement of biological information (FIG. 2) and at the time of the detection of an attached state (FIG. 3) is used as an electric signal detected by the R electrode 211R and is referred to as an "R detection signal 293R". Hereinafter, the C detection signal 293C, the L detection signal 293L, and the R detection signal 293R may be referred to as detection signals 293 where appropriate without discriminating the signals from one another.

The switching units 274 perform switching of at least some of the connections among at least one of the electrodes 211, the first signal applying unit 271, the second signal applying unit 272, and the relation detection unit 275 so that a first connection state at the time of the measurement of biological information (FIG. 2) and a second connection state at the time of the detection of an attached state (FIG. 3) are switched from one to another.

The first switching unit 274a selectively connects the C node 241C to one of the relay node 244 and the limiting circuit 273 in accordance with an instruction issued by the calculation processing device 230. At the time of the measurement of biological information (FIG. 2), when the first switching unit 274a connects the C node 241C to the relay node 244, the first signal applying unit 271 supplies the first applying signal 291 to the C electrode 211C. At the time of the detection of an attached state (FIG. 3), when the first switching unit 274a connects the C node 241C to the limiting circuit 273, the second signal applying unit 272 supplies the second applying signal 292 to the C electrode 211C.

The second switching unit 274b selectively connects the relation detection unit 275 to one of the C node 241C and the relay node 244 in accordance with an instruction issued by the calculation processing device 230. At the time of the measurement of biological information (FIG. 2), when the second switching unit 274b connects the relation detection unit 275 to the C node 241C, the C detection signal 293C is supplied to the relation detection unit 275. At the time of the detection of an attached state (FIG. 3), when the second switching unit 274b connects the relation detection unit 275 to the relay node 244, the first applying signal 291 is supplied to the relation detection unit 275.

The relation detection unit 275 includes a first differential amplifier 281, a first low-pass filter (LPF) 282, a second differential amplifier 283, and a second LPF 284. The relation detection unit 275 detects an L relation signal 294L and an R relation signal 294R (hereinafter collectively referred to as "relation signals 294" where appropriate) indicating the relative relationship (a difference in this embodiment) among a plurality of input electric signals.

The first differential amplifier 281 amplifies a change of the L detection signal 293L relative to a voltage supplied from the second switching unit 274b so as to generate an amplified signal. The first LPF 282 removes high-frequency noise of the amplified signal output from the first differential amplifier 281 so as to generate the L relation signal 294L to be supplied to the calculation processing device 230. The L relation signal 294L obtained at the time of the measurement of biological information (FIG. 2) indicates a difference between the C detection signal 293C and the L detection signal 293L based on the C detection signal 293C. The L relation signal 294L obtained at the time of the detection of an attached state (FIG. 3) indicates a difference between the first applying signal 291 and the L detection signal 293L based on the first applying signal 291.

The second differential amplifier 283 amplifies a change of the R detection signal 293R relative to a voltage supplied from the second switching unit 274b so as to generate an amplified signal. The second LPF 284 removes high-frequency noise of the amplified signal output from the second differential amplifier 283 so as to generate the R relation signal 294R to be supplied to the calculation processing device 230. The R relation signal 294R obtained at the time of the measurement of biological information (FIG. 2) indicates a difference between the C detection signal 293C and the R detection signal 293R based on the C detection signal 293C. The R relation signal 294R obtained at the time of the detection of an attached state (FIG. 3) indicates a difference between the first applying signal 291 and the R detection signal 293R based on the first applying signal 291.

Outline of Operation of Attached State Detection Unit

The attached state detection unit 231 detects an attached state of at least one of the electrodes 211 based on the relation signals 294 detected by the relation detection unit 275 at the time of the detection of an attached state. Since the relation signals 294 are generated based on the detection signals 293, the attached state detection unit 231 detects an attached state of at least one of the electrodes 211 based on the detection signal 293 detected by at least one of the electrodes 211 which is different from one of the electrodes 211 to which the second applying signal 292 is applied at the time of the detection of an attached state.

The attached state detection unit 231 at least temporarily stops the measurement of the biological information performed by the biological information measurement unit 232 when at least one of the L relation signal 294L and the R relation signal 294R satisfies a condition corresponding to an abnormal attached state at the time of the detection of an attached state. The attached state detection unit 231 starts the measurement of the biological information performed by the biological information measurement unit 232 when at least one of the L relation signal 294L and the R relation signal 294R satisfies a condition corresponding to a normal attached state at the time of the detection of an attached state.

Outline of Operation of Biological Information Measurement Unit

The biological information measurement unit 232 measures biological information (electrocardiogram in this embodiment) based on the L relation signal 294L detected by the relation detection unit 275 at the time of the measurement of biological information. The biological information measurement unit 232 measures the biological information based on the R relation signal 294R detected by the relation detection unit 275 at the time of the measurement of biological information. Since the relation signals 294 are generated based on the detection signals 293, the biological information measurement unit 232 measures the biological information based on the detection signal 293 detected by at least one of the electrodes 211 at the time of the measurement of biological information.

At least some of one or more electrodes 211 to which the first applying signal 291 is applied at the time of the measurement of biological information (that is, the C electrode 211C, the L electrode 211L, and the R electrode 211R) and one or more electrodes 211 in which the detection signals 293 is detected at the time of the measurement of biological information (that is, the C electrode 211C, the L electrode 211L, and the R electrode 211R) are the same as at least some of one or more electrodes 211 to which the second applying signal 292 is applied at the time of the detection of an attached state (that is, the C electrode 211C) and one or more electrodes 211 in which the detection signals 293 is detected at the time of the detection of an attached state (that is, the L electrode 211L and the R electrode 211R).

Method for Controlling Biological Information Measurement Apparatus

Figure 4:
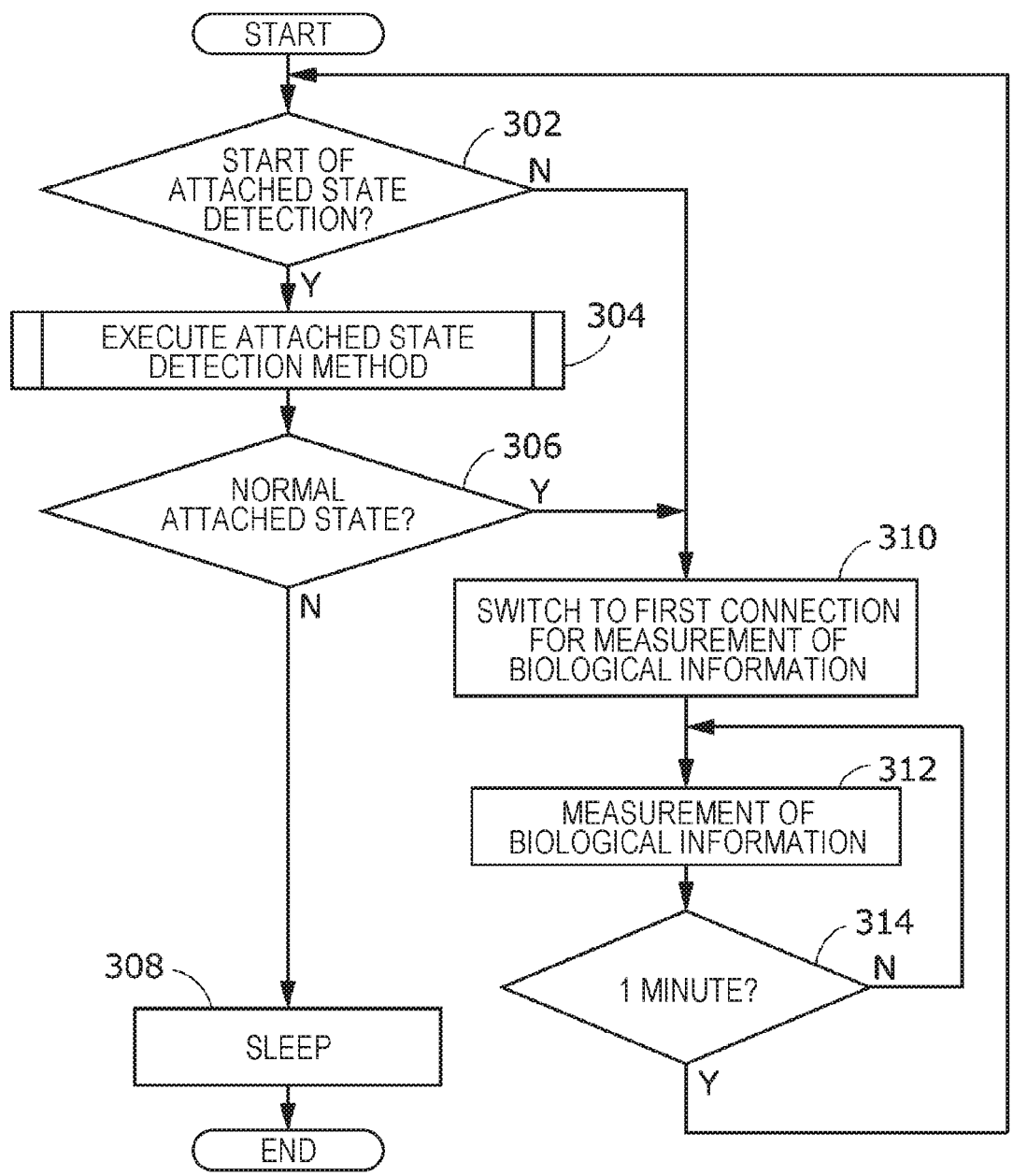
FIG. 4 is a flowchart for explaining a method for controlling the biological information measurement apparatus of FIG. 1.

FIG. 4 is a flowchart for explaining a method for controlling the biological information measurement apparatus 100 of FIG. 1. The control method of FIG. 4 will be described with reference to the configurations illustrated in FIGS. 2 and 3. For example, the control method is executed when power is turned on for the first time or in a predetermined cycle.

First, in step 302, the attached state detection unit 231 determines whether the detection of an attached state is to be started. In a case where a setting for starting the detection of an attached state has been performed, the attached state detection unit 231 determines that the detection of an attached state is to be started and the process proceeds to step 304. In a case where a setting for disabling the detection of an attached state has been performed, the attached state detection unit 231 determines that the detection of an attached state is not to be started and the process proceeds to step 310.

In step S304, the attached state detection unit 231 executes a method for detecting the attached state described below. In the attached state detection method, a normal attached state or an abnormal attached state is determined.

In the normal attached state, the C electrode 211C is in contact with the living body in the vicinity of the heart, the L electrode 211L is appropriately in contact with a portion on a left side of the C electrode 211C, the R electrode 211R is appropriately in contact with a portion on a right side of the C electrode 211C, and the L electrode 211L and the R electrode 211R are symmetrically disposed, for example. In the abnormal attached state, the C electrode 211C is shifted from the heart, at least one of the electrodes 211 is not sufficiently in contact with the living body, or the L electrode 211L and the R electrode 211R are not symmetrically disposed.

After step 304, the attached state detection unit 231 proceeds to step 308 when it is determined that a result of the determination performed by the attached state detection method indicates the abnormal attached state in step S306, whereas the attached state detection unit 231 proceeds to step 310 when it is determined that the result of the determination performed by the attached state detection method indicates the normal attached state in step 306.

In step 308, the attached state detection unit 231 causes the biological information measurement apparatus 100 to enter a sleep state and terminates the process. In the sleep state, the attached state detection unit 231 at least temporarily stops the measurement of biological information performed by the biological information measurement unit 232. In the sleep state, less power is consumed compared with the time when the biological information measurement is being performed. Specifically, the biological information may not be appropriately measured in the abnormal attached state, and therefore, electrical power is prevented from being unnecessarily consumed. In the sleep state, the attached state detection unit 231 periodically executes the control method so as to detect the normal attached state.

In step 310, the attached state detection unit 231 switches the switching units 274 to the first connection state (FIG. 2) for the measurement of biological information. After step 310, the attached state detection unit 231 proceeds to step 312.

Figure 6:
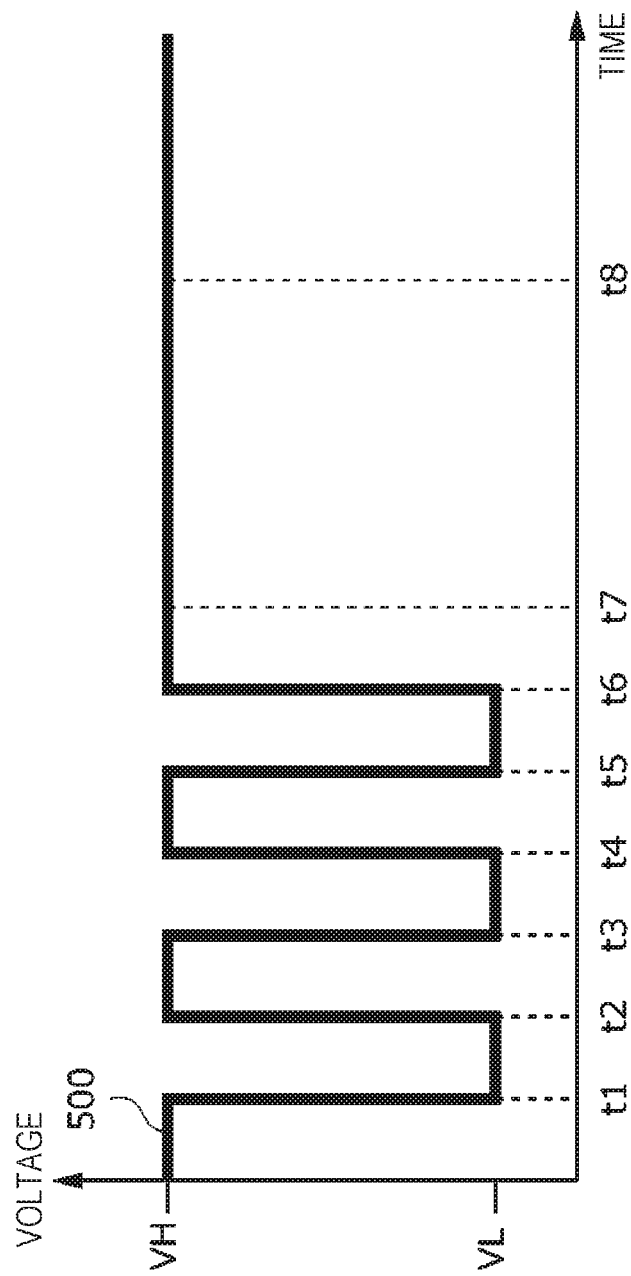
FIG. 6 is a graph illustrating an exemplary control signal which is output from a calculation processing apparatus illustrated in FIG. 2 and FIG. 3.

FIG. 6 is a graph illustrating an exemplary control signal 500 output from the attached state detection unit 231 to the first signal applying unit 271, the second signal applying unit 272, and the switching units 274. The control signal 500 is changed at the time of the detection of an attached state in a period from a time point t1 to a time point t7 as described below. When a length of a period of a high voltage value VH exceeds a threshold value as seen in a period from the time point t7 to a time point t8, the switching units 274 are switched to the first connection state (FIG. 2) after the time point t8, the second signal applying unit 272 stops the second applying signal 292, and the first signal applying unit 271 outputs the first applying signal 291. The first signal applying unit 271 supplies the first applying signal 291, that is, a direct current voltage, to the C electrode 211C, the L electrode 211L, and the R electrode 211R.

In step 312 of FIG. 4, the biological information measurement unit 232 measures biological information. At the time of the measurement of biological information, the first differential amplifier 281 amplifies a change of the L detection signal 293L relative to the C detection signal 293C so as to generate an amplified signal. The first LPF 282 removes high-frequency noise from the amplified signal generated by the first differential amplifier 281 so as to generate the L relation signal 294L. The biological information measurement unit 232 measures electrocardiogram information based on the L relation signal 294L.

The second differential amplifier 283 amplifies a change of the R detection signal 293R relative to the C detection signal 293C so as to generate an amplified signal. The second LPF 284 removes high-frequency noise from the amplified signal generated by the second differential amplifier 283 so as to generate the R relation signal 294R. The biological information measurement unit 232 measures electrocardiogram information of the living body based on the R relation signal 294R. After step 312, the biological information measurement unit 232 proceeds to step 314.

In step 314, the biological information measurement unit 232 returns to step 302 when one minute has elapsed since the first connection state (FIG. 2) for the measurement of biological information is started and returns to step 312 when one minute has not elapsed. Specifically, the biological information is continuously measured for one minute.

Attached State Detection Method

Figure 5:
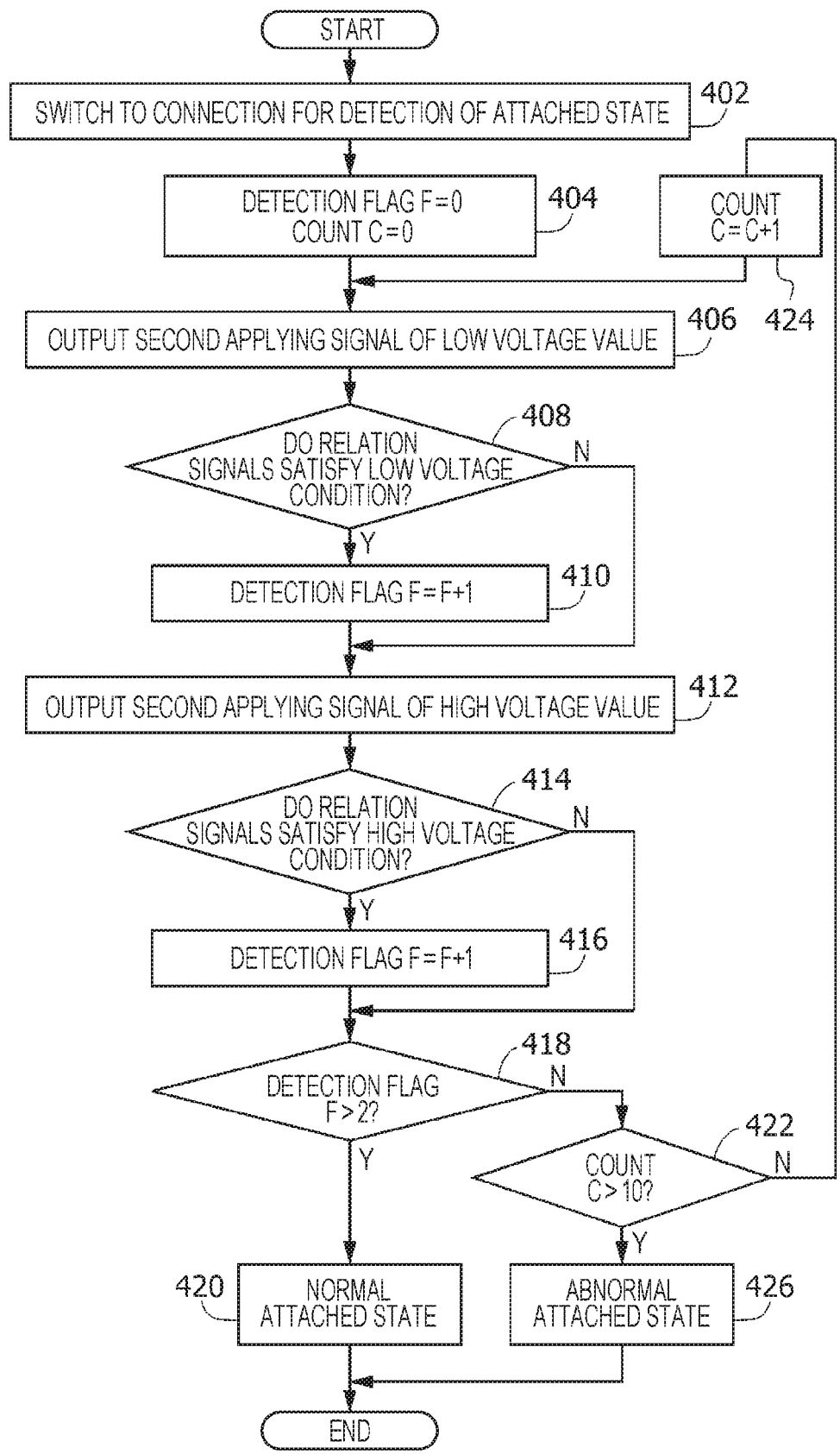
FIG. 5 is a flowchart for explaining a method for detecting an attached state of the biological information measurement apparatus of FIG. 1.

FIG. 5 is a flowchart of a method for detecting an attached state of the biological information measurement apparatus 100 of FIG. 1. The attached state detection method is executed in step 304 in the method for controlling the biological information measurement apparatus 100 illustrated in FIG. 4, for example.

First, in step 402 of FIG. 5, the attached state detection unit 231 switches the switching units 274 to the second connection state (FIG. 3) for the detection of an attached state. After step 402, the attached state detection unit 231 proceeds to step 404.

As illustrated in FIG. 6, when the control signal 500 is changed from a high voltage value VH to a low voltage value VL at a time point t1 after the first connection state (FIG. 2), the switching units 274 are switched to the second connection state (FIG. 3), the second signal applying unit 272 outputs the second applying signal 292, and the first signal applying unit 271 outputs the first applying signal 291. The second signal applying unit 272 applies the second applying signal 292 to the C electrode 211C. The second applying signal 292 is an alternate current voltage of a rectangular wave which is the same as the control signal 500 in the period from the time point t1 to the time point t7 illustrated in FIG. 6. The first signal applying unit 271 applies the first applying signal 291, that is, a direct current voltage, to the L electrode 211L and the R electrode 211R.

In step 404 of FIG. 5, the attached state detection unit 231 sets 0 to a detection flag F and 0 to a count C. The detection flag F is used to determine whether an attached state is normal. The count C indicates whether the number of times the detection flag F is consecutively checked. After step 404, the attached state detection unit 231 proceeds to step 406.

In step 406, the attached state detection unit 231 outputs the control signal 500 of the low voltage value VL in a period from the time point t1 to the time point t2 as illustrated in FIG. 6. The second signal applying unit 272 outputs the second applying signal 292 of the low voltage value VL which is the same as the control signal 500 in the period from the time point t1 to the time point t2. After step 406, the attached state detection unit 231 proceeds to step 408.

Figure 7:
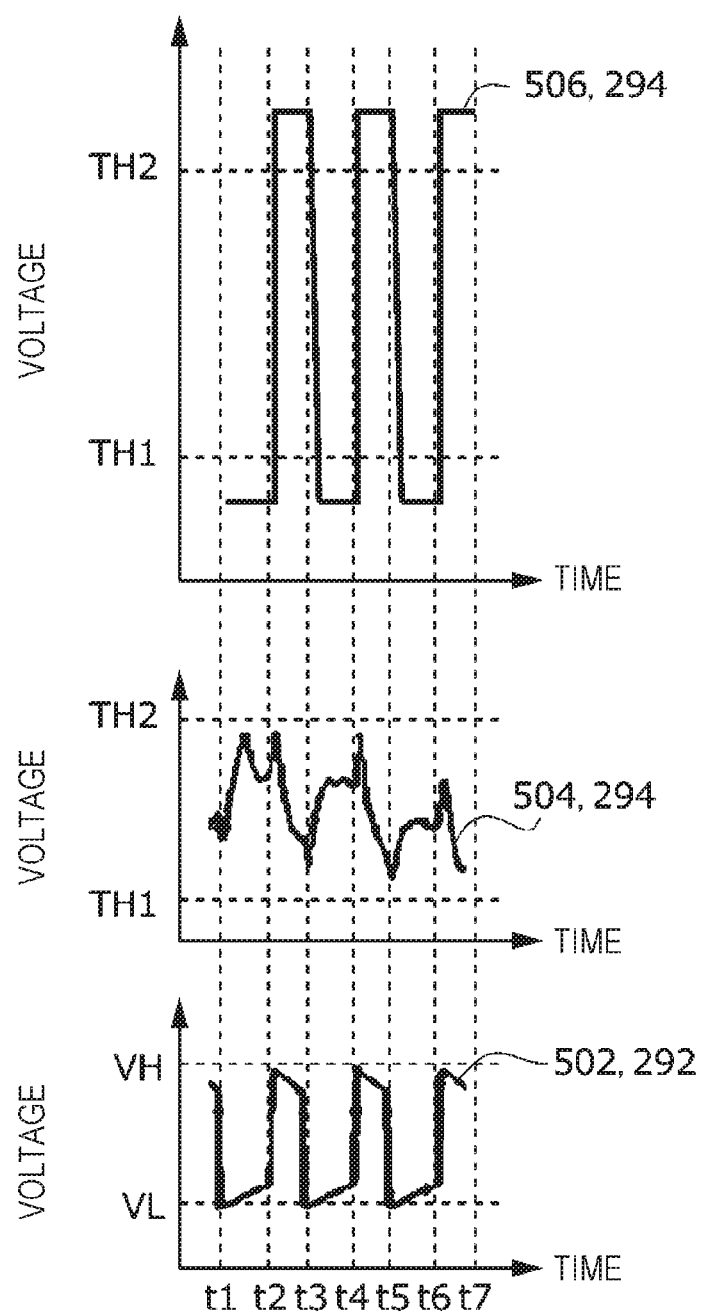
FIG. 7 is a diagram illustrating an exemplary measurement signal obtained by measuring a second applying signal and a relation signal of FIG. 3.

FIG. 7 is a diagram illustrating a first measurement signal 502, a second measurement signal 504, and a third measurement signal 506. The first measurement signal 502 is an exemplary signal obtained by measuring the second applying signal 292 applied to the C electrode 211C. The second measurement signal 504 is an exemplary signal obtained by measuring the L relation signal 294L when the L electrode 211L is separated from the living body.

The third measurement signal 506 is an exemplary signal obtained by measuring the L relation signal 294L when the L electrode 211L is appropriately in contact with the living body. To simplify the description, the R relation signal 294R is the same as the L relation signal 294L. The first measurement signal 502 changes similarly to the control signal 500 illustrated in FIG. 6.

In step 408 of FIG. 5, the attached state detection unit 231 determines whether the relation signals 294 satisfy a low voltage condition. When the low voltage condition is satisfied, the process proceeds to step 410, and otherwise, the process proceeds to step 412.

As indicated by the third measurement signal 506 of FIG. 7, the low voltage condition is satisfied when the L relation signal 294L and the R relation signal 294R are smaller than a threshold value TH1 for a predetermined period of time in the period from the time point t1 to the time point t2. As indicated by the second measurement signal 504, the low voltage condition is not satisfied unless at least one of the L relation signal 294L and the R relation signal 294R is smaller than the threshold value TH1 for the predetermined period of time in the period from the time point t1 to the time point t2.

In step 410 of FIG. 5, the attached state detection unit 231 increments the detection flag F by one. Specifically, when the low voltage condition is satisfied, the detection flag F is incremented by one, and otherwise, the detection flag F is not changed. After step 410, the attached state detection unit 231 proceeds to step 412.

In step 412, the attached state detection unit 231 outputs the control signal 500 of the high voltage value VH in a period from the time point t2 to the time point t3 as illustrated in FIG. 6. The second signal applying unit 272 outputs the second applying signal 292 of the high voltage value VH which is the same as the control signal 500 in the period from the time point t2 to the time point t3. After step 412, the attached state detection unit 231 proceeds to step 414.

In step 414, the attached state detection unit 231 determines whether the relation signals 294 satisfy a high voltage condition. When the high voltage condition is satisfied, the process proceeds to step 416, and otherwise, the process proceeds to step 418.

As indicated by the third measurement signal 506 of FIG. 7, the high voltage condition is satisfied when both the L relation signal 294L and the R relation signal 294R are larger than a threshold value TH2 for a predetermined period of time in the period from the time point t2 to the time point t3. As indicated by the second measurement signal 504, the high voltage condition is not satisfied unless at least one of the L relation signal 294L and the R relation signal 294R is larger than the threshold value TH2 for the predetermined period of time in the period from the time point t2 to the time point t3.

In step 416 of FIG. 5, the attached state detection unit 231 increments the detection flag F by one. Specifically, when the high voltage condition is satisfied, the detection flag F is incremented by one, and otherwise, the detection flag F is not changed. After step 416, the attached state detection unit 231 proceeds to step 418.

In step 418, when the detection flag F is larger than 2, the attached state detection unit 231 proceeds to step 420, and otherwise, the process proceeds to step 422.

In step S420, the attached state detection unit 231 determines that an attached state is normal. Specifically, when a sum of the number of times the low voltage condition is satisfied and the number of times the high voltage condition is satisfied exceeds 2, it is determined that an attached state is normal. After step 420, the attached state detection unit 231 terminates the attached state detection method.

In step 422, when the count C is not larger than 10, the attached state detection unit 231 proceeds to step 424, and otherwise, the attached state detection unit 231 proceeds to step 426.

In step 424, the attached state detection unit 231 increments the count C by one and returns to step 406. As indicated in a period from the time point t3 to the time point t7 of FIG. 6, the control signal 500 repeatedly performs the change that is the same as that in the period from the time point t1 to the time point t3 in a period from the time point t3 to the time point t5 and a period from the time point t5 to the time point t7 until the attached state detection method is terminated. The number of times the repetition is performed may be larger than 3 or smaller than 3.

In step 426 of FIG. 5, the attached state detection unit 231 determines that an attached state is abnormal. Specifically, when the sum of the number of times the low voltage condition is satisfied and the number of times the high voltage condition is satisfied does not exceed 2 after a sequence of the determination of the low voltage condition and the determination of the high voltage condition is repeatedly performed 12 times, it is determined that an attached state is abnormal. After step 426, the attached state detection unit 231 terminates the attached state detection method.

As indicated by the exemplary control signal 500 of FIG. 6, when terminating the attached state detection method, the attached state detection unit 231 outputs the high voltage value VH for a period of time which exceeds a threshold value after the time point t7.

Although both the L relation signal 294L and the R relation signal 294R are used for the determination of the low voltage condition and the high voltage condition in this embodiment, only one of the L relation signal 294L and the R relation signal 294R may be used. An attached state of at least one of the C electrode 211C and the L electrode 211L may be determined based on the L relation signal 294L. An attached state of at least one of the C electrode 211C and the R electrode 211R may be determined based on the R relation signal 294R. The low voltage condition and the high voltage condition may be determined using a signal obtained by adding the L relation signal 294L and the R relation signal 294R to each other.

In the normal attached state, the C electrode 211C is in contact in the vicinity of the heart and the L electrode 211L and the R electrode 211R are symmetrically disposed with respect to the C electrode 211C as the center. Accordingly, in the normal attached state, the L relation signal 294L and the R relation signal 294R have waveforms similar to each other. The attached state detection unit 231 may determine that an attached state is normal when a difference between the L relation signal 294L and the R relation signal 294R is equal to or smaller than a threshold value and determine that an attached state is abnormal when the difference between the L relation signal 294L and the R relation signal 294R is larger than the threshold value.

Figure 8:
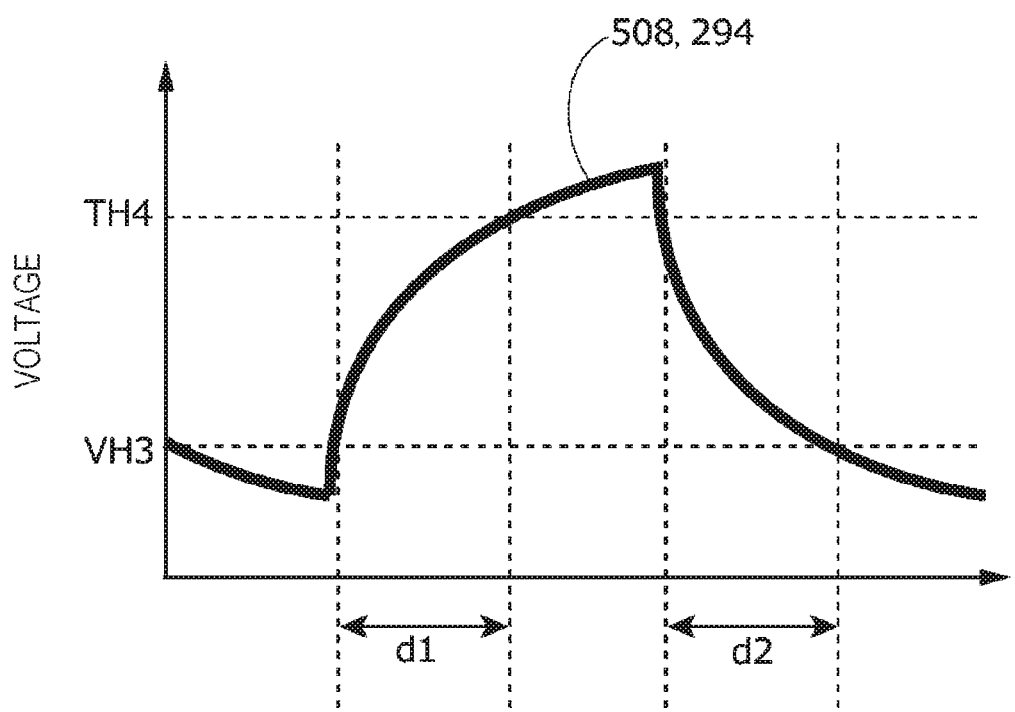
FIG. 8 is a diagram illustrating an exemplary measurement signal obtained by measuring the relation signal of FIG. 3.

FIG. 8 is a diagram illustrating an exemplary fourth measurement signal 508 obtained by measuring the relation signals 294 when the electrodes 211 are appropriately in contact with the living body. At the time of the detection of an attached state, the attached state detection unit 231 may detect an attached state based on at least one of a rising time d1 and a falling time d2 of the relation signals 294. Since resistances between the electrodes 211 and the living body are small in the normal attached state, the rising time d1 and the falling time d2 of the fourth measurement signal 508 are short. In a case where the electrode 211 is partially or entirely separated from the living body, a large resistance is obtained, and therefore, the rising time d1 and the falling time d2 of the fourth measurement signal 508 are long.

For example, when the control signal 500 rises at the time point t2 illustrated in FIG. 6, if the rising time d1 in a change of the fourth measurement signal 508 from a low voltage threshold value TH3 to a high voltage threshold value TH4 of FIG. 8 is equal to or smaller than a threshold value, it is determined that an attached state is normal, and otherwise, it is determined that an attached state is abnormal. For example, when the control signal 500 falls at the time point t3 illustrated in FIG. 6, if the falling time d2 in a change of the fourth measurement signal 508 from the high voltage threshold value TH4 to the low voltage threshold value TH3 of FIG. 8 is equal to or smaller than a threshold value, it is determined that an attached state is normal, and otherwise, it is determined that an attached state is abnormal.

According to this embodiment, in the biological information measurement apparatus 100 in which the first applying signal 291 is applied to the living body when the biological information is measured and the second applying signal 292 is applied to the living body when an attached state is detected, the electrodes 211 are used in common at the time of the measurement of biological information and the detection of an attached state, and therefore, an attached state may be automatically detected with a simple configuration when compared with a case where dedicated electrodes 211 are provided. By detecting an attached state, reliability of measurement data is enhanced, and therefore, biological information may be measured with high accuracy with a simple configuration and less operation by a user.

According to this embodiment, with the simple configuration in which the first connection state (FIG. 2) and the second connection state (FIG. 3) are switched from one to another by the switching units 274, the electrodes 211 may be used in common at the time of the measurement of biological information and the detection of an attached state.

According to this embodiment, with the simple configuration in which the first connection state (FIG. 2) and the second connection state (FIG. 3) are switched from one to another by the switching units 274, the relation detection unit 275 may be used in common at the time of the measurement of biological information and the detection of an attached state.

According to this embodiment, the attached state may be detected with a simple configuration by detecting rounding of the detection signals 293 which has passed through the living body using at least one of the rising time and the falling time of a signal indicating a difference between the first applying signal 291 and the detection signals 293.

According to this embodiment, the measurement of the biological information may be at least temporarily stopped based on the attached state, and therefore, unrequired measurement of the biological information in an abnormal attached state may be avoided and wasteful power consumption may be suppressed.

According to this embodiment, the measurement of the biological information may be automatically started based on the attached state, and therefore, complicated operations to be performed by the user may be eliminated and usability may be enhanced.

According to this embodiment, the attached state of the electrodes 211 may be accurately detected without mistakenly recognizing the second applying signal 292 as a noise signal.

Second Embodiment

Figure 9:
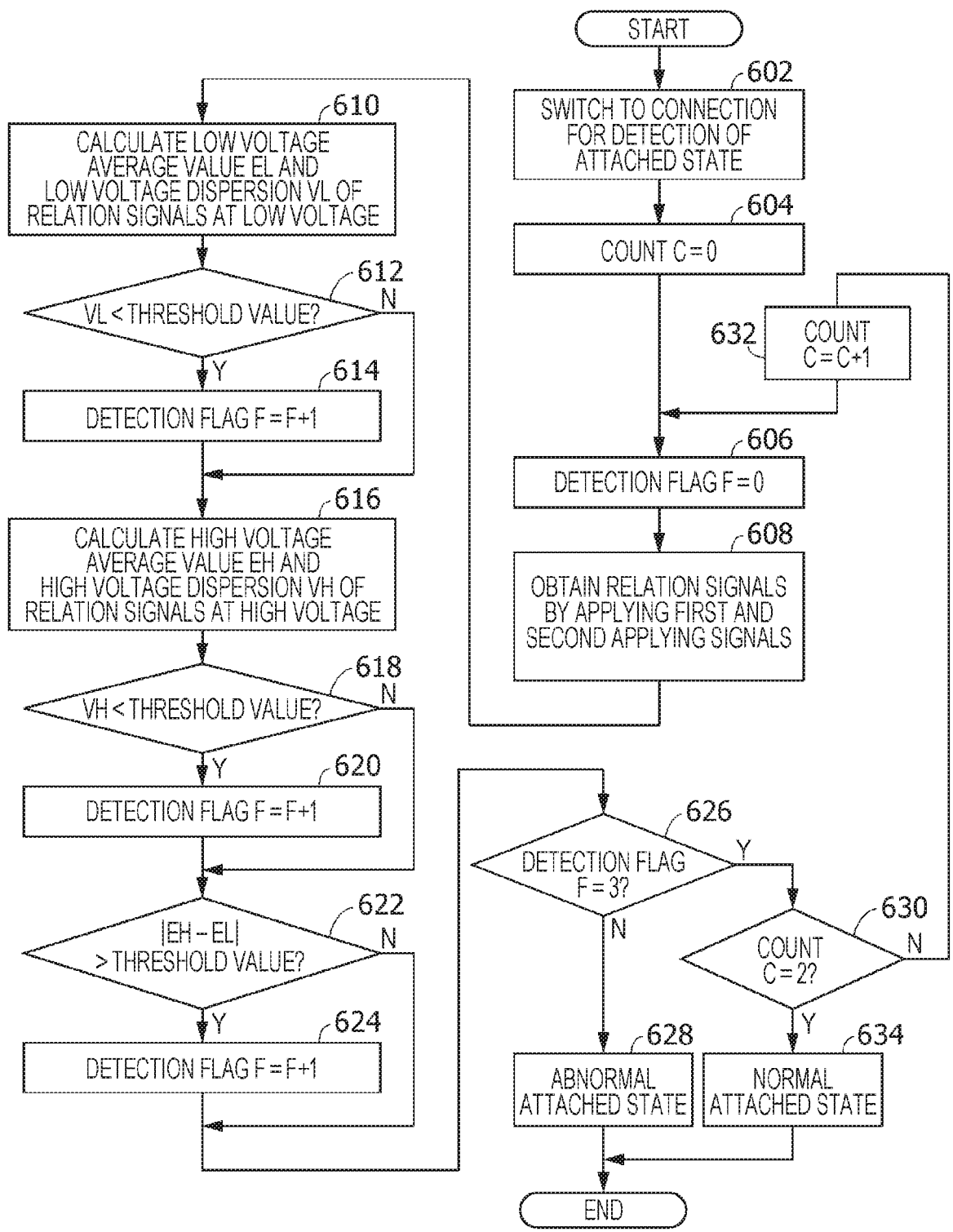
FIG. 9 is a flowchart for explaining a method for detecting an attached state according to a second embodiment.

Next, a method for detecting an attached state according to a second embodiment will be described. FIG. 9 is a flowchart for explaining a method for detecting an attached state according to this embodiment. The method for detecting an attached state in this embodiment is executed by the biological information measurement apparatus 100 illustrated in FIG. 3 according to the first embodiment and executed in step 304 of the control method according to the first embodiment illustrated in FIG. 4, for example. Hereinafter, FIG. 3 of the first embodiment is mainly referred to when components are referred to.

Figure 10:
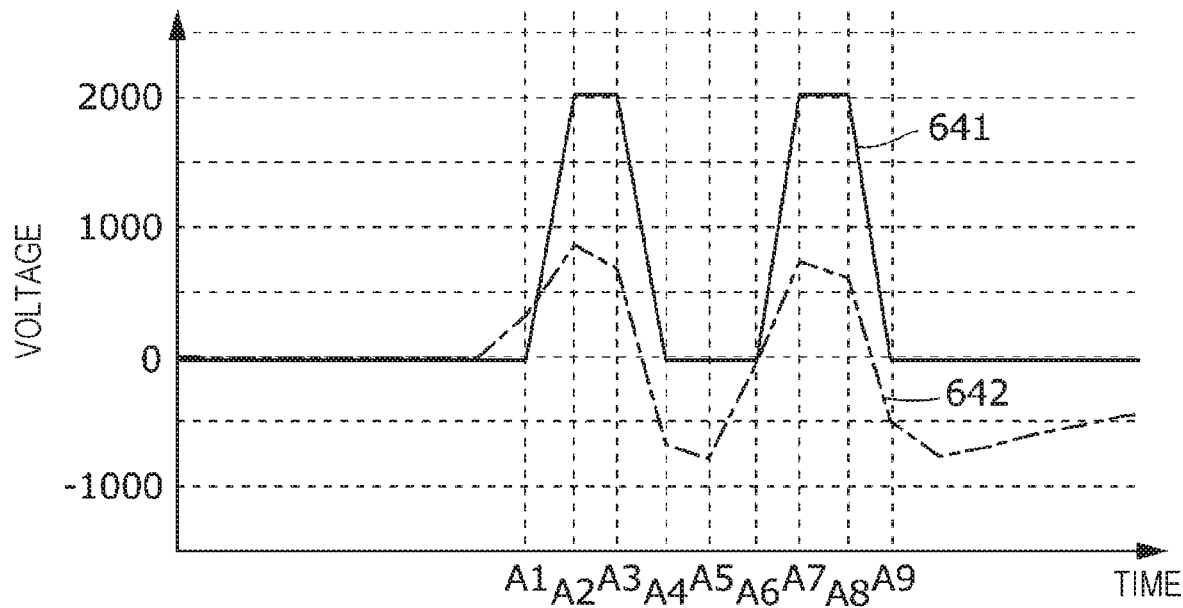
FIG. 10 is a graph illustrating an exemplary applying signal and a first exemplary relation signal of a first example.

FIG. 10 is a graph illustrating an exemplary applied signal 641 indicating the second applying signal 292 of a first example and a first exemplary relation signal 642 indicating the L relation signal 294L obtained when the exemplary applied signal 641 is applied in the first example. The first example corresponds to a normal attached state in which the L electrode 211L is appropriately in contact with the living body.

Figure 11:
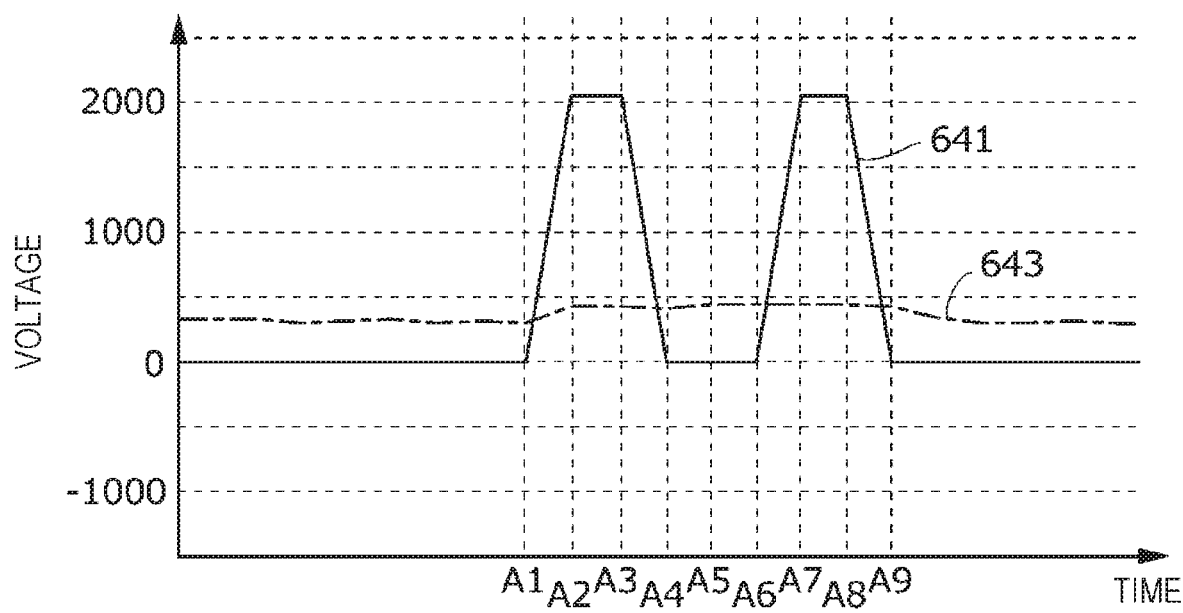
FIG. 11 is a graph illustrating an exemplary applying signal and a second exemplary relation signal of a second example.

FIG. 11 is a graph illustrating an exemplary applied signal 641 indicating the second applying signal 292 of a second example and a second exemplary relation signal 643 indicating the L relation signal 294L obtained when the exemplary applied signal 641 is applied in the second example. The exemplary applied signal 641 of the second example is the same as the exemplary applied signal 641 of the first example. The second example corresponds to an abnormal attached state in which the L electrode 211L is separated from the living body.

Figure 12:
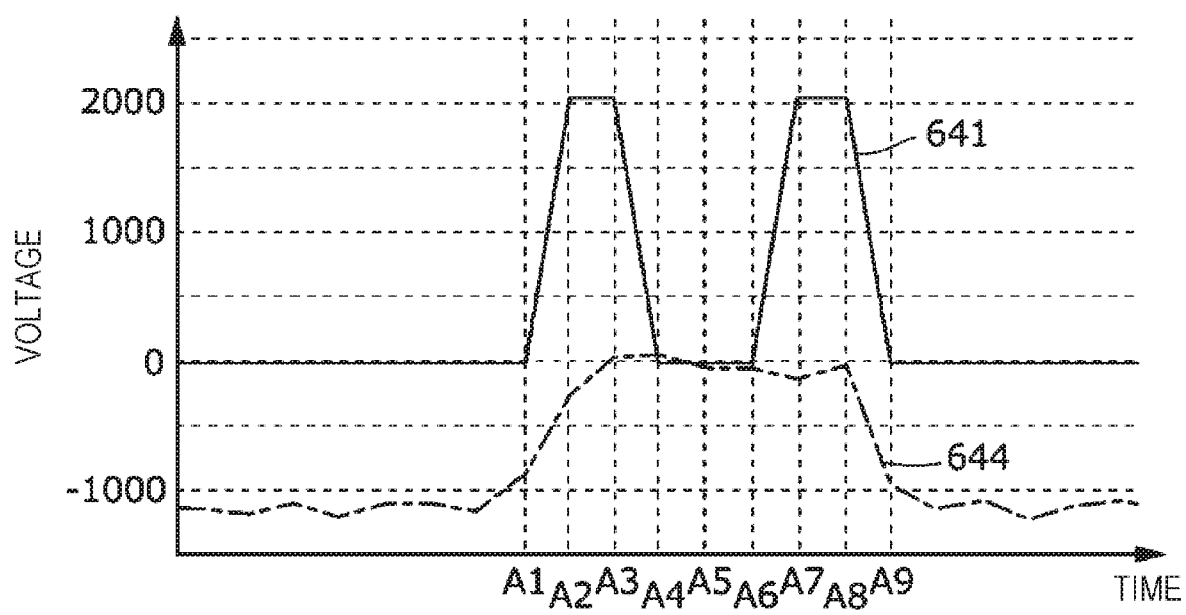
FIG. 12 is a diagram illustrating the exemplary applying signal and a third exemplary relation signal of the second example.

FIG. 12 is a graph illustrating an exemplary applied signal 641 indicating the second applying signal 292 of a third example and a third exemplary relation signal 644 indicating the L relation signal 294L obtained when the exemplary applied signal 641 is applied in the third example. The exemplary applied signal 641 of the third example is the same as the exemplary applied signal 641 of the first example. The third example corresponds to an abnormal attached state in which the L electrode 211L is separated from the living body. In the third example, noise larger than that of the second example is included in a third exemplary relation signal 644.

Although the attached state detection method according to this embodiment will be described hereinafter with reference to FIGS. 10 to 12, the examples of FIGS. 10 to 12 may not cover all cases. In FIGS. 10 to 12, axes of abscissae indicate time and axes of ordinates indicate a voltage in an arbitrary unit. Although only the attached state of the L electrode 211L is described in this embodiment, the same is true of the R electrode 211R.

First, in step 602 of FIG. 9, the attached state detection unit 231 switches the switching units 274 into the second connection state for the detection of an attached state (FIG. 3). After step 602, the method proceeds to step 604.

In step 604 of FIG. 9, the attached state detection unit 231 sets 0 to the count C. As described below, the count C indicates the number of times a condition for a normal attached state is satisfied. After step 604, the method proceeds to step 606.

In step 606 of FIG. 9, the attached state detection unit 231 sets 0 to the detection flag F. As described below, the detection flag F is used to determine whether an attached state is normal. After step 606, the method proceeds to step 608.

In step 608 of FIG. 9, the attached state detection unit 231 controls the first signal applying unit 271 so that the first applying signal 291 is output as a direct current voltage. The first applying signal 291 is applied to the L electrode 211L and the R electrode 211R and further supplied to the first differential amplifier 281 and the second differential amplifier 283.

Furthermore, in step 608, the attached state detection unit 231 controls the second signal applying unit 272 so that the second applying signal 292 is output. The second applying signal 292 is applied to the C electrode 211C and transmitted to a human body.

The exemplary applied signal 641 illustrated in FIG. 10 which is the exemplary second applying signal 292 is approximately 0 before a time point A1 and after a time point A9. Specifically, the exemplary applied signal 641 is applied in a period from the time point A1 to the time point A9 and is not applied in other periods.

The exemplary applied signal 641 linearly rises from a low voltage value of approximately 0 at the time point A1 to a high voltage value of approximately 2000 at the time point A2, the substantially constant high voltage value is maintained in a period from the time point A2 to the time point A3, the high voltage value of approximately 2000 at the time point A3 linearly falls to the low voltage value of approximately 0 at the time point A4, and the substantially constant low voltage value is maintained in a period from the time point A4 via the time point A5 to the time point A6.

Furthermore, the exemplary applied signal 641 linearly rises from the low voltage value of approximately 0 at the time point A6 to a high voltage value of approximately 2000 at the time point A7, the substantially constant high voltage value is maintained in a period from the time point A7 to the time point A8, and the high voltage value of approximately 2000 at the time point A8 linearly falls to the low voltage value of approximately 0 at the time point A9. A waveform of the exemplary applied signal 641 in a period from the time point A1 to the time point A4 is substantially the same as a waveform of the exemplary applied signal 641 in a period from the time point A6 to the time point A9. Specifically, the exemplary applied signal 641 includes at least one combination of a period in which a low voltage value is applied and a period in which a high voltage value is applied.

In step 608 of FIG. 9, the attached state detection unit 231 obtains the relation signals 294 by applying the first applying signal 291 and the second applying signal 292. The relation signals 294 are obtained at time points having labels between the time point A1 to the time point A9 illustrated in FIGS. 10 to 12. After step 608, the attached state detection unit 231 proceeds to step 610.

As illustrated in FIG. 10, in the normal attached state, the first exemplary relation signal 642 changes substantially in accordance with a change of the exemplary applied signal 641. Specifically, the first exemplary relation signal 642 has comparatively high values in a period from the time point A2 to the time point A3 and a period from the time point A7 to the time point A8 and a comparatively low value in a period from the time point A4 to the time point A6. The first exemplary relation signal 642 has two peaks as a whole.

As illustrated in FIG. 11, in an abnormal attached state in which noise is small, the second exemplary relation signal 643 is hardly affected by the change of the exemplary applied signal 641 and is substantially constant in a value in a range from approximately 0 to approximately 500. As illustrated in FIG. 12, in an abnormal attached state in which noise is large, the third exemplary relation signal 644 is considerably affected by the change of the exemplary applied signal 641 when compared with the example illustrated in FIG. 11. Specifically, the third exemplary relation signal 644 has a high value in the period from the time A1 to the time A9 when compared with other periods. The third exemplary relation signal 644 has one peak as a whole.

In step 610 of FIG. 9, the attached state detection unit 231 calculates a low voltage average value EL and a low voltage dispersion VL of the relation signals 294 obtained when the second applying signal 292 has a low voltage. In FIGS. 10 to 12, the second applying signal 292 has a low voltage in the period from the time point A4 to the time point A6.

In step 612 of FIG. 9, the attached state detection unit 231 determines whether the low voltage dispersion VL is smaller than a low voltage threshold value, that is, whether the low voltage dispersion VL satisfies a first condition. When the first condition is satisfied, the relation signals 294 changed substantially in accordance with the second applying signal 292 at a time of a low voltage. When the first condition is satisfied, it is likely that an attached state is normal. Therefore, after the detection flag F is incremented by one in step 614, this method proceeds to step 616. When the first condition is not satisfied, an attached state is abnormal and the method proceeds to step 616.

In the normal attached state in FIG. 10, values of the relation signals 294 in a low voltage are in a range from approximately −800 to approximately 0, and the values do not include local maximum values before and after the values although the values are slightly shifted. Accordingly, it is determined that the low voltage dispersion VL is smaller than the low voltage threshold value. The values of the relation signals 294 in a low voltage are not considerably changed even in the abnormal attached state illustrated in FIGS. 11 and 12, and therefore, it is determined that the low voltage dispersion VL is smaller than the low voltage threshold value.

In step 616 of FIG. 9, the attached state detection unit 231 calculates a high voltage average value EH and a high voltage dispersion VH of the relation signals 294 obtained when the second applying signal 292 has a high voltage. In FIGS. 10 and 12, the second applying signal 292 has a high voltage in the period from the time point A2 to the time point A3 and the period from the time point A7 to the time point A8.

In step 618 of FIG. 9, the attached state detection unit 231 determines whether the high voltage dispersion VH is smaller than a high voltage threshold value, that is, whether the high voltage dispersion VH satisfies a second condition. When the second condition is satisfied, the relation signals 294 changes substantially in accordance with the second applying signal 292 at a time of a high voltage. When the second condition is satisfied, it is likely that an attached state is normal. Therefore, after the detection flag F is incremented by one in step 620, this method proceeds to step 622. When the second condition is not satisfied, an attached state is abnormal and the method proceeds to step 622.

In the normal attached state in FIG. 10, values of the relation signals 294 in a high voltage are in a range from approximately 500 to approximately 1000, and the values do not include local minimum values before and after the values although the values are slightly shifted. Accordingly, it is determined that the high voltage dispersion VH is smaller than the high voltage threshold value. Although the values of the relation signals 294 in the high voltage are not considerably changed even in the abnormal attached state illustrated in FIGS. 11 and 12, and therefore, it is determined that the high voltage dispersion VH is smaller than the high voltage threshold value.

In step 622 of FIG. 9, the attached state detection unit 231 determines whether an absolute value of a difference between a high voltage average value EH and a low voltage average value EL is larger than an absolute threshold value, that is, whether a third condition is satisfied. When the third condition is satisfied, the relation signals 294 change substantially in accordance with the second applying signal 292 which is changed between when a low voltage is applied and when a high voltage is applied. When the third condition is satisfied, it is likely that the normal attached state is attained. Therefore, after the detection flag F is incremented by one in step 624, this method proceeds to step 626. When the third condition is not satisfied, it is determined that an attached state is abnormal and the method proceeds to step 626.

In the normal attached state of FIG. 10, the absolute value of the difference is approximately 1500 which is determined to be larger than the absolute threshold value. In the abnormal attached state of FIG. 11, the absolute value of the difference is as small as approximately 100 which is determined not to be larger than the absolute threshold value. In the abnormal attached state of FIG. 12, the absolute value of the difference is as small as approximately 400 which is determined not to be larger than the absolute threshold value.

In step 626, the attached state detection unit 231 determines whether the detection flag F is 3. As the detection flag F is closer to 3, it is highly likely that the relation signals 294 are changed in accordance with the change of the second applying signal 292 and an attached state is normal.

When it is determined that the detection flag F is not 3 in step 626, the attached state detection unit 231 determines that the attached state is abnormal in step 628 and the method is terminated. When the detection flag F is not 3, at least one of the first to third conditions is not satisfied.

When it is determined that the detection flag F is 3 in step 626, the method proceeds to step 630. When the detection flag F is 3, all the first to third conditions are satisfied.

In step 630, the attached state detection unit 231 determines whether the count C is 2. The count C indicates the number of times it is determined that it is highly likely that an attached state is normal. When it is determined that the count C is not 2 in step 630, the attached state detection unit 231 increments the count C by one in step 632 and the process in step 606 onwards is executed again. When it is determined that the count C is 2 in step 630, the attached state detection unit 231 determines that an attached state is normal in step 634 and the method is terminated.

Summary

According to this embodiment, the effect similar to that in the first embodiment is also obtained in this embodiment except for the different points of the attached state detection method.

According to this embodiment, the second applying signal 292 includes at least one combination of a period in which a low voltage value is applied and a period in which a high voltage value which is higher than the low voltage value is applied. The attached state detection unit 231 calculates the low voltage average value EL indicating an average value of the relation signals 294 when the low voltage value is applied and the low voltage dispersion VL indicating dispersion of the relation signals 294 when the low voltage value is applied. The attached state detection unit 231 calculates the high voltage average value EH indicating an average value of the relation signals 294 when the high voltage value is applied and the high voltage dispersion VH indicating dispersion of the relation signals 294 when the high voltage value is applied. The attached state detection unit 231 determines that an attached state is normal when the first condition indicating that the low voltage dispersion VL is smaller than the low voltage threshold value, the second condition indicating that the high voltage dispersion VH is smaller than the high voltage threshold value, and the third condition indicating that the absolute value of the difference between the low voltage average value EL and the high voltage average value EH is larger than the absolute threshold value and determines that an attached state is abnormal when at least one of the first to third conditions is not satisfied. Accordingly, the change of the relation signals 294 in accordance with the second applying signal 292 may be accurately determined when compared with a case where one of the conditions is not used for the determination.

The present invention is not limited to the foregoing embodiments. Specifically, those who skilled in the art may perform various changes, combinations, sub-combinations, and replacement on the components of the foregoing embodiments within the scope of the invention and within an equivalent range.

The present invention is applicable to various biological information measurement apparatuses attached to a living body, such as a biological information measurement apparatus used for electrocardiographic measurement, ocular potential measurement, or myopotential measurement.

What is claimed is:
1. A biological information measurement apparatus comprising:
   a plurality of electrodes each configured to be attached to a living body so as to obtain an electric signal from the living body;
   a first signal applying unit configured to provide a first input signal, the first input signal being applied to at least one of the plurality of electrodes during a measurement of biological information;
   a biological information measurement unit configured to measure the biological information based on a detection signal detected by the at least one electrode during the measurement of biological information;
   a second signal applying unit configured to apply a second input signal to at least one of the plurality of electrodes during a detection of a state of attachment of at least one of the plurality of electrodes to the living body;
   an attached state detection unit configured to detect the state of attachment based on the detection signal detected by at least one of the plurality of electrodes which is different from the at least one electrode to which the second input signal is applied during the detection of the state of attachment;
   a switching unit configured to perform switching among at least part of connections among the plurality of electrodes, the first signal applying unit, and the second signal applying unit; and a relation detection unit configured to detect a relation signal indicating a relative relationship among a plurality of input signals, wherein at least some of the at least one electrode to which the first input signal is applied during the measurement of biological information and the at least one electrode with which the detection signal is detected during the measurement of biological information are same electrodes as at least some of the at least one electrode to which the second input signal is applied during the detection of the state of attachment and the at least one electrode with which the detection signal is detected during the detection of the state of attachment, wherein the plurality of electrodes include a first electrode and a second electrode, wherein the switching unit performs switching between a first connection state in which the first input signal is applied to the first electrode during the measurement of biological information, and a second connection state in which the second input signal is applied to the first electrode during the detection of the state of attachment, wherein the switching unit changes at least part of connections among the plurality of electrodes, the first signal applying unit, the second signal applying unit, and the relation detection unit, such that the detection signal detected by the first electrode and the detection signal detected by the second electrode are supplied to the relation detection unit in the first connection state, and that the first input signal and the detection signal detected by the second electrode are supplied to the relation detection unit in the second connection state, wherein the relation detection unit detects a first relation signal indicating a relative relationship between the detection signal detected by the first electrode and the detection signal detected by the second electrode during the measurement of biological information, and a second relation signal indicating the relative relationship between the first input signal and the detection signal detected by the second electrode during the detection of the state of attachment, wherein the biological information measurement unit measures the biological information based on the first relation signal, and wherein the attached state detection unit detects the state of attachment based on the second relation signal.

2. The biological information measurement apparatus according to claim 1, wherein the second input signal includes at least one combination of a first period in which the second input signal has a low voltage and a second period in which the second input signal has a high voltage higher than the low voltage, wherein the attached state detection unit is further configured to calculate:

a low voltage average value indicating an average value of the second relation signals and a low voltage dispersion indicating a dispersion of the second relation signals for the second relation signals which are obtained when the second input signal has the low voltage; and a high voltage average value indicating an average value of the second relation signals and a high voltage dispersion indicating a dispersion of the second relation signals for the second relation signals which are obtained when the second input signal has the high voltage, and wherein the attached state detection unit determines that the state of attachment is normal if a first condition indicating that the low voltage dispersion is smaller than a predetermined low voltage threshold value, a second condition indicating that the high voltage dispersion is smaller than a predetermined high voltage threshold value, and a third condition indicating that an absolute value of a difference between the low voltage average value and the high voltage average value is larger than an absolute threshold value are all satisfied, while the attached state detection unit determines that the state of attachment is abnormal if at least one of the first to third conditions is not satisfied.

3. The biological information measurement apparatus according to claim 1, wherein the attached state detection unit is further configured to stop, at least temporarily, the measurement of biological information by the biological information measurement unit, if the detection signal obtained during the detection of the state of attachment satisfies a condition corresponding to an abnormal state of attachment.

4. The biological information measurement apparatus according to claim 1, wherein the attached state detection unit is further configured to start the measurement of biological information by the biological information measurement unit if the detection signal obtained during the detection of the state of attachment satisfies a condition corresponding to a normal state of attachment.

5. The biological information measurement apparatus according to claim 1, wherein the second input signal has a signal waveform which is different from a signal waveform of a noise signal.

6. The biological information measurement apparatus according to claim 1, wherein the first input signal is a direct current voltage signal, and the second input signal has a rectangular waveform, and wherein the attached state detection unit detects the state of attachment based at least on one of arising time and a falling time of a signal indicating a difference between the first input signal and the detection during the detection of the state of attachment.

7. The biological information measurement apparatus according to claim 1, wherein the attached state detection unit is further configured to stop, at least temporarily, the measurement of biological information by the biological information measurement unit, if the detection signal obtained during the detection of the state of attachment satisfies a condition corresponding to an abnormal state of attachment.

8. The biological information measurement apparatus according to claim 1, wherein the attached state detection unit is further configured to start the measurement of biological information by the biological information measurement unit if the detection signal obtained during the detection of the state of attachment satisfies a condition corresponding to a normal state of attachment.

9. The biological information measurement apparatus according to claim 1, wherein the second input signal has a signal waveform which is different from a signal waveform of a noise signal.

10. A method for controlling a biological information measurement apparatus including a plurality of electrodes to be attached to a living body so as to obtain an electric signal from the living body, the method comprising:

applying a first input signal from a first signal applying unit to at least one of the electrodes during measurement of biological information;

measuring the biological information based on a detection signal detected by the at least one electrode during the measurement of biological information;

applying a second input signal from a second signal applying unit to at least one of the electrodes during a detection of a state of attachment of at least one of the electrodes to the living body; and detecting the state of attachment based on the detection signal detected by at least one of the electrodes which is different from the at least one electrode to which the second input signal is applied during the detection of the state of attachment, wherein at least some of the at least one electrode to which the first input signal is applied during the measurement of biological information and the at least one electrode with which the detection signal is detected during the measurement of biological information are same electrode as at least some of the at least one electrode to which the second input signal is applied during the detection of the state of attachment and the at least one electrode with which the detection signal is detected during the detection of the state of attachment, wherein the biological measurement apparatus further includes a switching unit for performing switching among at least part of connections among the plurality of electrodes, the first signal applying unit, and the second signal applying unit, and the plurality of electrodes include a first electrode and a second electrode, and wherein the method further comprises:

using the switching unit, witching between a first connection state in which the first input signal is applied to the first electrode during the measurement of biological information, and a second connection state in which the second input signal is applied to the first electrode during the detection of the state of attachment;

applying the first input signal to the first electrode and the second electrode during the measurement of biological information;

detecting a first relation signal indicating a relative relationship between the detection signal detected by the first electrode and the detection signal detected by the second electrode during the measurement of biological information;

measuring the biological information based on the first relation signal;

supplying the first input signal during the detection of the state of attachment;

applying the second input signal to the first electrode during the detection of the state of attachment, the second input signal not being applied to the second electrode during the detection of the state of attachment;

detecting a second relation signal indicating the relative relationship between the first input signal and the detection signal detected by the second electrode during the detection of the state of attachment; and detecting the state of attachment based on the second relation signal.

11. The method according to claim 10, wherein the second input signal includes at least one combination of a first period in which the second input signal has a low voltage and a second period in which the second input signal has a high voltage higher than the low voltage, the method further comprising:

calculating a low voltage average value indicating an average value of the second relation signals and a low voltage dispersion indicating a dispersion of the second relation signals for the second relation signals which are obtained when the second input signal has the low voltage;

calculating a high voltage average value indicating an average value of the second relation signals and a high voltage dispersion indicating a dispersion of the second relation signals for the second relation signals which are obtained when the second input signal has the high voltage;

determining that the state of attachment is normal if a first condition indicating that the low voltage dispersion is smaller than a predetermined low voltage threshold value, a second condition indicating that the high voltage dispersion is smaller than a predetermined high voltage threshold value, and a third condition indicating that an absolute value of a difference between the low voltage average value and the high voltage average value is larger than an absolute threshold value are all satisfied; and determining that the state of attachment is abnormal if at least one of the first to third conditions is not satisfied.

12. A method for controlling a biological information measurement apparatus including a plurality of electrodes to be attached to a living body so as to obtain an electric signal from the living body, the method comprising:

applying a first input signal to at least one of the electrodes during measurement of biological information;

measuring the biological information based on a detection signal detected by the at least one electrode during the measurement of biological information;

applying a second input signal to at least one of the electrodes during a detection of a state of attachment of at least one of the electrodes to the living body; and detecting the state of attachment based on the detection signal detected by at least one of the electrodes which is different from the at least one electrode to which the second input signal is applied during the detection of the state of attachment, wherein at least some of the at least one electrode to which the first input signal is applied during the measurement of biological information and the at least one electrode with which the detection signal is detected during the measurement of biological information are same electrode as at least some of the at least one electrode to which the second input signal is applied during the detection of the state of attachment and the at least one electrode with which the detection signal is detected during the detection of the state of attachment, wherein the first input signal is a direct current voltage signal, and the second input signal has a rectangular waveform, and the detecting the detecting the state of attachment includes:

detecting the state of attachment based on at least one of a rising time and a falling time of a signal indicating a difference between the first input signal and the detection signal during the detection of the state of attachment.

13. The method according to claim 12, further comprising:

stopping, at least temporarily, the measurement of biological information, if the detection signal obtained during the detection of the state of attachment satisfies a condition corresponding to an abnormal state of attachment; and starting the measurement of biological information if the detection signal obtained during the detection of the state of attachment satisfies a condition corresponding to a normal state of attachment.

14. A biological information measurement apparatus comprising:
a plurality of electrodes each configured to be attached to a living body so as to obtain an electric signal from the living body;
a first signal applying unit configured to provide a first input signal, the first input signal being applied to at least one of the plurality of electrodes during a measurement of biological information;
a biological information measurement unit configured to measure the biological information based on a detection signal detected by the at least one electrode during the measurement of biological information;
a second signal applying unit configured to apply a second input signal to at least one of the plurality of electrodes during a detection of a state of attachment of at least one of the plurality of electrodes to the living body; and
an attached state detection unit configured to detect the state of attachment based on the detection signal detected by at least one of the plurality of electrodes which is different from the at least one electrode to which the second input signal is applied during the detection of the state of attachment,
wherein at least some of the at least one electrode to which the first input signal is applied during the measurement of biological information and the at least one electrode with which the detection signal is detected during the measurement of biological information are same electrodes as at least some of the at least one electrode to which the second input signal is applied during the detection of the state of attachment and the at least one electrode with which the detection signal is detected during the detection of the state of attachment,
wherein the first input signal is a direct current voltage signal, and the second input signal has a rectangular waveform,
and wherein the attached state detection unit detects the state of attachment based on at least one of a rising time and a falling time of a signal indicating a difference between the first input signal and the detection signal during the detection of the state of attachment.

15. The biological information measurement apparatus according to claim 14, wherein the attached state detection unit is further configured to stop, at least temporarily, the measurement of biological information by the biological information measurement unit, if the detection signal obtained during the detection of the state of attachment satisfies a condition corresponding to an abnormal state of attachment.

16. The biological information measurement apparatus according to claim 14, wherein the attached state detection unit is further configured to start the measurement of biological information by the biological information measurement unit if the detection signal obtained during the detection of the state of attachment satisfies a condition corresponding to a normal state of attachment.

17. The biological information measurement apparatus according to claim 14, wherein the second input signal has a signal waveform which is different from a signal waveform of a noise signal.

18. A biological information measurement apparatus comprising:
a plurality of electrodes each configured to be attached to a living body so as to obtain an electric signal from the living body;
a first signal applying unit configured to provide a first input signal, the first input signal being applied to at least one of the plurality of electrodes during a measurement of biological information;
a biological information measurement unit configured to measure the biological information based on a detection signal detected by the at least one electrode during the measurement of biological information;
a second signal applying unit configured to apply a second input signal to at least one of the plurality of electrodes during a detection of a state of attachment of at least one of the plurality of electrodes to the living body;
an attached state detection unit configured to detect the state of attachment based on the detection signal detected by at least one of the plurality of electrodes which is different from the at least one electrode to which the second input signal is applied during the detection of the state of attachment;
a switching unit configured to perform switching among at least part of connections among the plurality of electrodes, the first signal applying unit, and the second signal applying unit,
wherein at least some of the at least one electrode to which the first input signal is applied during the measurement of biological information and the at least one electrode with which the detection signal is detected during the measurement of biological information are same electrodes as at least some of the at least one electrode to which the second input signal is applied during the detection of the state of attachment and the at least one electrode with which the detection signal is detected during the detection of the state of attachment,
wherein the plurality of electrodes include a first electrode,
wherein the switching unit performs switching between a first connection state in which the first input signal is applied to the first electrode during the measurement of biological information, and a second connection state in which the second input signal is applied to the first electrode during the detection of the state of attachment,
wherein the first input signal is a direct current voltage signal, and the second input signal has a rectangular waveform,
and wherein the attached state detection unit detects the state of attachment based on at least one of a rising time and a falling time of a signal indicating a difference between the first input signal and the detection signal during the detection of the state of attachment.

* * * * *